United States Patent [19]
Hoffmockel et al.

[11] Patent Number: 6,124,480
[45] Date of Patent: Sep. 26, 2000

[54] PROCESS FOR PREPARING TRIOXANE

[76] Inventors: Michael Hoffmockel, Feldbergblick 11, D-65527, Niedernhausen; Günter Sextro, Erbsenacker 37, D-65207, Wiesbaden; Gerhard Emig, Vogelherd 157, D-91058, Erlangen; Frank Kern, Just-Strasse 79, D-76870, Kandel, all of Germany

[21] Appl. No.: 08/496,954

[22] Filed: Jun. 30, 1995

[30] Foreign Application Priority Data

Jul. 6, 1994 [DE] Germany .............................. 44 23 618

[51] Int. Cl.$^7$ .................................................. C07D 323/06
[52] U.S. Cl. .......................................................... 549/368
[58] Field of Search .............................................. 549/368

[56] References Cited

U.S. PATENT DOCUMENTS 3,496,192  2/1970  Ackermann et al. ................... 260/340
4,381,397  4/1983  Yoshida et al. .......................... 549/368

FOREIGN PATENT DOCUMENTS

| 252 913 | 3/1967 | Austria . |
| 604 884 | 7/1994 | European Pat. Off. . |
| 606 056 | 7/1994 | European Pat. Off. . |
| 31 06 476 | 12/1981 | Germany . |
| 59-25387 | 2/1984 | Japan . |

OTHER PUBLICATIONS

Akimoto, M. et al 12—Heteropolymolybdates as catalysts for vapor–phase oxidative dehydrogenation of isobutyric acid. 3. Molybdotungstophosphoric and molybdovanadophosphoric acids. CA102:12784 (1984).

*Primary Examiner*—Amelia Owens

[57] ABSTRACT

The process serves for the preparation of trioxane from formaldehyde in the gas phase in the presence of a tungstomolybdophosphoric acid of the composition $H_3PW_nMo_mO_{40} \cdot xH_2O$ (n=4–8, m=12-n; x=0–32) as catalyst.

11 Claims, 1 Drawing Sheet

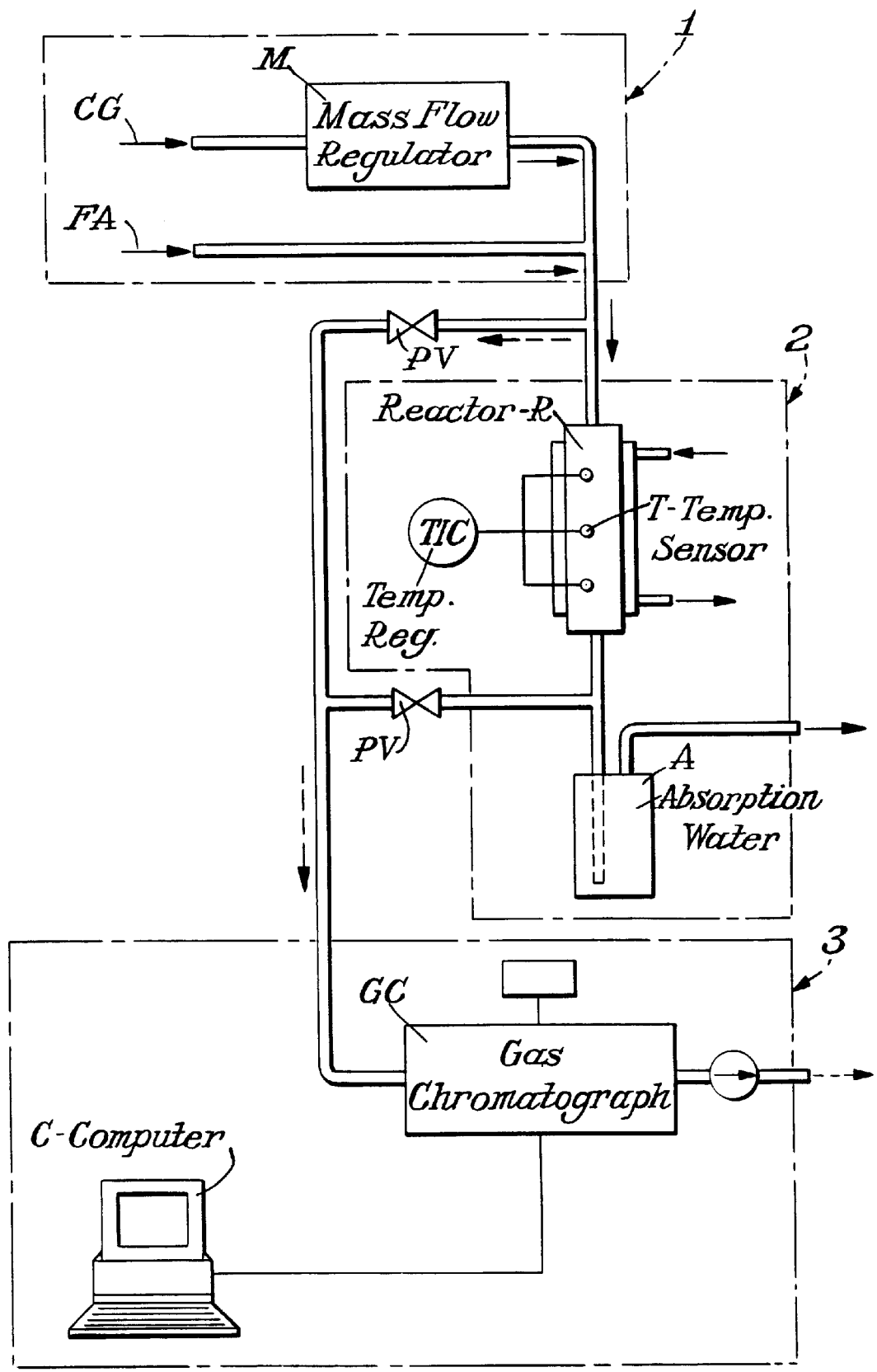

PROCESS FOR PREPARING TRIOXANE

FIELD OF INVENTION

The invention relates to a process for the continuous preparation of trioxane in the gas phase by heterogeneous catalysis. tungstomolybdophosphoric acids of the composition.

DESCRIPTION OF THE PRIOR ART

Trioxane can be prepared from aqueous formaldehyde solutions using acid catalysts. A characteristic of these processes is the high energy consumption for evaporating water which is introduced into the process by the starting material streams.

Various proposals exist for preparing trioxane by a gas-phase trimerization of formaldehyde, but in many cases use is made of formaldehyde streams of differing water content. When water-containing formaldehyde is used, problems occur due to deposition of polyoxymethylene on the catalyst surface.

A process for preparing trioxane by means of an acid ion exchange resin is known (DE-C-1 593 990). Likewise known is a catalyst for the gas-phase trimerization in the form of phosphoric acid or sulfuric acid on $SiO_2$ supports (AT-B 252 913). In addition, various heteropolyacids have been used as catalysts in the gas-phase trimerization of formaldehyde (JP-A 59-25387). In these processes, the yields are not satisfactory.

Progress has been achieved by the use of so-called anhydrous formaldehyde, i.e. formaldehyde having water contents $\leq 1\%$. In this way, the deposits of polyoxymethylene on the catalyst surface can be reduced or prevented and the yields can also be increased. Trimerization catalysts in the form of vanadyl hydrogen phosphate (EP 93 120 599) and the heteropolyacid 1-vanado-11-molybdophosphoric acid ($H_4PVMo_{11}O_{40}$) (1-V acid) (EP 941 00010) are known. However, these catalysts are still not satisfactory with regard to a high conversion and simultaneously high selectivity.

SUMMARY OF THE INVENTION

It is an object of the invention to eliminate this disadvantage.

This object is achieved by a process which is distinguished from the known processes by the catalyst which leads to a high selectivity and at the same time to a conversion which is close to the thermodynamically possible conversion.

The invention provides a process for preparing trioxane from formaldehyde in the gas phase in the presence of a catalyst of the formula $H_3PW_nMo_mO_{40} \cdot xH_2O$ (n=4 to 8, m=12-n, x=0 to 32) (hereinafter referred to as MoW acid).

These heteropolyacids serving as catalysts can be prepared by the method of WU (J. Biol. Chem. 43 (1920) 189).

BRIEF DESCRIPTION OF THE DRAWING

The sole Figure of the Drawing is a schematic illustration of an apparatus suitable for carrying out the process of this invention and for analyzing and evaluating the results of the process.

DETAILED DESCRIPTION

The catalyst can be used by itself or with pressing aids. Unsupported catalysts can be prepared by mixing sieved MoW acid (particle size, for example, 150 μm) with the desired amount of pressing aid and subsequently pressing into pellets of the desired size. The pressing aids used are materials which are inert in the reaction, e.g. finely divided silica ($SiO_2$), aluminum oxide or hydroxide. The use of the catalyst on a support material is advantageous. Support materials which can be used are inert materials, e.g. pellets of silicon carbide, silicon dioxide or aluminum oxide.

The formaldehyde used in this process can have a small water content, i.e. contain up to 1% by weight of water. Preference is given to formaldehyde having a residual water content of up to 50 ppm, which is generally referred to as anhydrous formaldehyde. If the gas stream contains no water, the catalyst is present under the reaction conditions in anhydrous form or as hexahydrate.

The temperature range for the reaction is usually from 80 to 150° C. Preference is given to the range from 100 to 120° C.

The contact duration at which few byproducts (<4%) are formed is from 1 to 30 seconds, preferably from 1 to 10 seconds. Longer contact times are possible, but then there is the risk of increased byproduct formation.

The reaction is influenced by the partial pressure of formaldehyde. The catalyst has a high selectivity for the formation of trioxane over a wide pressure range. The inlet partial pressure of formaldehyde is generally from 0.5 to 5 bar, preferably from 0.5 to 2 bar.

The catalysts for preparing trioxane were tested in an apparatus as is schematically shown in the Figure. The apparatus comprises three parts:

Metering in 1

Formation reactor 2

Analysis and evaluation 3

For the test, formaldehyde FA is introduced into the apparatus and, if desired, mixed with a carrier gas CG. Carrier gases which can be used are hydrogen, noble gases such as helium, argon, krypton or xenon, preference is given to using nitrogen.

The carrier gas can be added to the formaldehyde inlet stream by means of a thermal mass flow regulator M. Use of variable amounts of carrier gas for diluting the formaldehyde inlet stream enables the desired partial pressures of formaldehyde to be set in a simple manner.

The formaldehyde gas stream was passed into the reactor R containing the catalyst. The temperature in the reactor was regulated by means of a thermostat or temperature regulator TIC and was measured at three different points along the catalyst bed (radial) by temperature sensors T. Silicone oil was used as heat transfer medium. Other heat transfer media such as mineral oils can likewise be used. The temperatures were recorded and give information about the stable operating state of the reactor during an experiment.

The outlet stream leaving the reactor and containing the reaction products formed was collected by absorption (A) using water. The trioxane formed can be isolated therefrom in a known manner by extraction.

To determine the conversion, the gas composition of the inlet and outlet streams of the reactor were determined on-line. Samples were here taken automatically during operation via pneumatic ball valves (PV) and analyzed in a gas chromatograph (GC). Sampling was carried out at regular intervals, e.g. every ten minutes, and was controlled by means of a computer e.

The equilibrium conversion ($C_{eq}$) is calculated from the prevailing partial pressures and the equilibrium constants of Busfield and Merigold ("The Gas-Phase Equilibrium between Trioxane and Formaldehyde", J. Am. Chem. Soc.

(A), 1969, p. 2975). The ratio of the experimentally determined conversion $C_{exp}$ to the equilibrium conversion gives the relative conversion $C_{rel}$.

Relative conversion $C_{rel}=100 \cdot C_{exp}/C_{eq}$.

The arrangement of the apparatus for the process of the invention and the dimensions can be matched to the respective conditions.

In the process of the invention, the following advantages are worthy of particular emphasis:

1. Achievement of high space-time yields (STY) [kg/m$^3$·h],
2. no byproducts,
3. moderate heat generation in the synthesis reactor.

EXAMPLES

In all the examples presented, nitrogen was used as carrier gas and reference gas for the analyses. The water content of the formaldehyde inlet stream was below 50 ppm.

The MoW acids serving as catalyst were prepared by the method of WU (loc. cit.).

To prepare the impregnated catalysts, the MoW acid, dissolved in water, is used for soaking or impregnating the supports. For this purpose, the catalyst supports are covered with the solution, the air present in the pores of the supports is drawn off by reducing the pressure in the impregnation vessel, the supernatant solution is poured off and the impregnated supports are dried at 373K in air. If the supports are only to be soaked, the evacuation can be omitted.

In the following examples, MoW acids impregnated on SiC supports were used.

The formation reactor comprised a stainless steel tube reactor having a length of 150 mm and an internal diameter of 16 mm.

The results of the following experiments are given in Table 1.

1) 0.56 g of the catalyst $H_3PW_4Mo_8O_{40}$ on 18.12 g of SiC pellets (diameter 3 mm, height 3 mm) was used in the reactor. The inlet partial pressure of formaldehyde was 790 bar. The volume of the catalyst bed was 20 cm$^3$. The contact time was 6.2 seconds.

2) 0.62 g of the catalyst $H_3PW_6Mo_6O_{40}$ on 18.14 g of SiC pellets (diameter 3 mm, height 3 mm) was used in the reactor. The inlet partial pressure of formaldehyde was 780 mbar. The volume of the catalyst bed was 20 cm$^3$. The contact time was 6.5 seconds.

3) 0.53 g of the catalyst $H_3PW_8Mo_4O_{40}$ on 18.02 g of SiC pellets (diameter 3 mm, height 3 mm) was used in the reactor. The inlet partial pressure of formaldehyde was 802 mbar. The volume of the catalyst bed was 20 cm$^3$. The contact time was 6.0 seconds.

Comparative examples follow.

4) 0.645 g of the catalyst $H_3PW_2Mo_{10}O_{40}$ on 18.15 g of SiC pellets (diameter 3 mm, height 3 mm) was used in the reactor. The inlet partial pressure of formaldehyde was 818 mbar. The volume of the catalyst bed was 20 cm$^3$. The contact time was 6.25 seconds.

5) 0.535 g of the catalyst $H_3PW_{10}Mo_2O_{40}$ on 18.27 g of SiC pellets (diameter 3 mm, height 3 mm) was used in the reactor. Methyl formate and small amounts of trimethyl orthoformate were formed as byproducts. The inlet partial pressure of formaldehyde was 780 mbar. The volume of the catalyst bed was 20 cm$^3$. The contact time was 6.4 seconds.

6) 0.563 g of the catalyst 1-V acid on 16.7 g of cylindrical SiC pellets (diameter 6 mm, height 6 mm) was used in the reactor. The inlet partial pressure of formaldehyde was 1150 mbar, the volume of the catalyst bed was 16.6 cm$^3$. The residence time was 5.1 seconds.

7) 0.9 of the catalyst 1-V acid on 26.65 g of cylindrical SiC pellets )diameter 6 mm, height 6 mm) was used in the reactor. The inlet partial pressure of formaldehyde was 950 mbar, the volume of the catalyst bed was 26.7 cm$^3$. the residence time was 5.1 seconds.

TABLE 1

Experimental results of the Examples 1 to 5 and the Comparative Examples 6 and 7 (reaction temperature: 383 K.)

| Example (Temp. 383 K.) | Catalyst | n°$_{form}$ mol/h | Selectivity/1 | $C_{exp}$ % | $C_{rel}$ % | STY kg·m$^{-3}$·h$^{-1}$ |
|---|---|---|---|---|---|---|
| 1 | $H_3PW_4Mo_8O_{40}$ | 0.25 | 1 | 25.2 | 91 | 94.5 |
| 2 | $H_3PW_6Mo_6O_{40}$ | 0.23 | 0.995 | 24.9 | 93.8 | 85.9 |
| 3 | $H_3PW_8Mo_4O_{40}$ | 0.26 | 0.965 | 28.5 | 100 | 107.2 |
| 4* | $H_3PW_2Mo_{10}O_{40}$ | 0.215 | 1 | 14.7 | 53.5 | 47.5 |
| 5* | $H_3PW_{10}Mo_2O_{40}$ | 0.23 | 0.85 | 30.6 | 100 | 89.8 |
| 6* | $H_4PVMo_{11}O_{40}$ | 0.386 | 1 | 29.6 | 81.3 | 206.8 |
| 7* | $H_4PVMo_{11}O_{40}$ | 0.375 | 1 | 13.67 | 45.5 | 57.6 |

*Comparative examples
n°$_{form}$ [mol/h] - formaldehyde inlet flow
n$_{form}$ [mol/h] - formaldehyde outlet flow
STY [kg/m$^3$ · h] - space-time yield of trioxane
$C_{exp}$ [%] - experimental conversion $C_{exp} = 100 \cdot (n°_{form} - n_{form}/n°_{form})$
$C_{rel}$ [%] - relative conversion The catalysts of the invention show no deactivation at a test duration of 300 hours.

As shown by the Examples 1 to 3, the MoW acids of the invention possess both high selectivities for the formation of trioxane and high conversions close to the equilibrium conversion, combined with high space-time yields.

In the Comparative Examples 4 and 5, use is made of MoW acids which have a different composition from the MoW acids of the invention. These give either a high selectivity at a low relative conversion (Example 4) or a high conversion at a low selectivity (Example 5). These examples clearly show that not every MoW acid as catalyst leads to a high conversion at a high selectivity.

Comparative Examples 6 and 7 serve as comparison with another catalyst system, viz. 1-vanado-11-molybdophosphoric acid. The catalyst system gives high selectivities but only moderate relative conversions.

In Comparative Example 7, which, at a formaldehyde inlet partial pressure of 950 mbar, is most comparable with the Examples 1 to 3 (about 800 mbar), both the relative conversion and the space-time yield are significantly lower. Additionally increasing the inlet partial pressure to 1150 mbar enabled improvements to be achieved (Example 6). However, higher pressures are always associated with a greater risk of formation of deposits of polyoxymethylene.

We claim:

1. A process for preparing trioxane, comprising:
    converting formaldehyde to trioxane, in the gas phase, in the presence of a catalyst comprising a tungstomolybdophosphoric acid of the composition

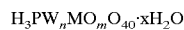

$H_3PW_nMO_mO_{40} \cdot xH_2O$ where n ranges from 4 to 8, m ranges from 4 to 8, n+m=12, and x ranges from 0 to 32.

2. The process as claimed in claim 1, wherein said catalyst has been applied to an inert support material.

3. The process as claimed in claim 1, wherein said catalyst has been applied to a support material comprising silicon carbide.

4. The process as claimed in claim 1, wherein said formaldehyde has a water content of less than 1% by weight.

5. The process as claimed in claim 1, wherein the converting of formaldehyde to trioxane is carried out at a temperature in the range of 80 to 150° C.

6. The process as claimed in claim 1, wherein said formaldehyde is in brought into contact with said catalyst for period of time ranging from 1 to 30 seconds.

7. The process as claimed in claim 1, wherein, at the beginning of said converting step, said formaldehyde has a partial pressure ranging from 0.5 to 5 bar.

8. The process as claimed in claim 1, wherein said converting of formaldehyde to trioxane is carried out in the presence of a carrier gas.

9. The process as claimed in claim 8, wherein said carrier gas comprises nitrogen.

10. The process as claimed in claim 8, wherein said formaldehyde is mixed with said carrier gas prior to said converting step to provide an inlet gas stream for said converting step.

11. The process as claimed in claim 10, wherein, in the resulting inlet gas stream, the formaldehyde has a partial pressure of 0.5 to 5 bar.

* * * * *